United States Patent [19]

Frohning et al.

[11] 4,368,142

[45] Jan. 11, 1983

[54] METHANATION CATALYST

[75] Inventors: Dieter Frohning; Gerhard Horn, both of Oberhausen, Fed. Rep. of Germany

[73] Assignee: Ruhrchemie Aktiengesellschaft, Oberhausen, Fed. Rep. of Germany

[21] Appl. No.: 220,381

[22] Filed: Dec. 29, 1980

[30] Foreign Application Priority Data

Dec. 29, 1979 [DE] Fed. Rep. of Germany ....... 2952683

[51] Int. Cl.$^3$ .......................... B01J 21/12; B01J 21/04; B01J 21/10; B01J 23/76
[52] U.S. Cl. ................................ 252/455 R; 252/457; 252/459; 252/466 J; 252/473; 518/717
[58] Field of Search .................... 252/455 R, 457, 459, 252/466 J, 473; 518/717

[56] References Cited

U.S. PATENT DOCUMENTS

| | | | |
|---|---|---|---|
| 2,219,042 | 10/1940 | Heckel et al. | 518/717 X |
| 2,702,814 | 2/1955 | Riblett et al. | 518/717 |
| 2,852,570 | 9/1958 | Conradin et al. | 252/473 X |
| 3,156,657 | 11/1964 | Pinder et al. | 518/717 X |
| 3,451,949 | 6/1969 | Topsoe et al. | 252/455 R |
| 3,549,556 | 12/1970 | Dienes | 252/455 R |
| 3,945,944 | 3/1976 | Kang | 252/455 R |
| 4,022,810 | 5/1977 | Kobylinski et al. | 252/459 X |
| 4,217,295 | 8/1980 | Friedrich et al. | 518/717 X |

*Primary Examiner*—Carl F. Dees
*Attorney, Agent, or Firm*—Sprung, Horn, Kramer & Woods

[57] ABSTRACT

A methanation catalyst comprising cobalt, nickel and magnesium, disposed on a carrier; a process for its preparation and use of the catalyst for methanation.

17 Claims, No Drawings

METHANATION CATALYST

BACKGROUND OF THE INVENTION

1. Field of the Invention

This invention relates to catalysts which contain nickel and cobalt as active constituents in combination with MgO as promoter, and a carrier, as well as a process for their preparation. The catalysts are particularly suitable for hydrogenation carbon monoxide mainly into methane in a fluidized bed method.

2. Discussion of Prior Art

The shortage of natural gas in the foreseeable future has led to the development of various processes for the catalytic hydrogenation of carbon monoxide. Such processes are aimed at producing a synthetic gas (Substitute Natural Gas or SNG) which is largely equivalent to natural gas as regards composition and utilizability and is thus able to replace the latter. Natural gas frequently contains, in addition to methane, also ethane, propane or even butane in amounts of up to a total of about 0.1 to 5.0% by volume referred to the content of methane. These hydrocarbons raise the calorific value of the gas and are, therefore, desirable within certain limits. However, they effect the density, burning and combustion properties of the gas, with the result that their content must be kept within specific limits.

The processes for the catalytic hydrogenation of carbon monoxide to methane principally differ by the measures used to remove the heat of reaction liberated during the methanation. In most multi-stage processes the catalysts are arranged in a stationary system. Recent process developments use the fluidized bed technique for the methanation, since in this way particularly high space-time yields can be obtained and at the same time the thermal stress to which the catalyst is subjected is kept within bounds by virtue of the good heat transfer. Examples of the catalytic hydrogenation of carbon monoxide into mainly methane using the fluidized bed technique are given in German Offenlegungsschriften Nos. 2,449,587; 2,651,567 and 2,807,422.

The hydrogenation of carbon monoxide into mainly methane is catalyzed by nickel, ruthenium, cobalt or iron. Catalysts for technical requirements contain almost exclusively nickel as active main component, the nickel content normally amounting to 30 to 40% of the total weight of the catalysts. Cobalt is little used as active main component for methanation catalysts since, like iron, it has substantial disadvantages compared with nickel, the main disadvantage being the tendency to increased carbon deposition. The use of ruthenium, which possesses excellent properties for the hydrogenation of carbon oxides, has not hitherto been adopted on a technical scale.

In addition to hydrogenation-active metals, methanation catalysts normally contain additions of difficultly reducible oxides, which are used as electron or structural promoters, or also as carrier materials or constituents of carrier materials.

It is known to use nickel and cobalt together on carrier as a catalyst for hydrogenating carbon monoxide. Thus, the preparation of a catalyst preproduct containing nickel and cobalt oxides by precipitation is described in German Offenlegungsschrift No. 2 621 314. The catalyst obtained from the preproduct contains more than 40% by weight of nickel oxide and cobalt oxide and is used in the form of a catalyst fixed bed for the methanation.

German Offenlegungsschrift No. 2 631 901 concerns a catalyst for methanation according to the fixed bed method, which catalyst may also contain in addition to nickel as the active main component, cobalt, iron, copper, magnesium, zinc, aluminum and chromium. This catalyst is prepared by combined precipitation of the components as silicates, which have a composition comparable to that of natural minerals (serpentine). In addition to the metal silicates, this catalyst contains argillaceous minerals. The content of nickel or nickel and cobalt in the catalyst is 65% by weight. Details as to how and in what way the properties of the catalyst can be influenced by adding cobalt and/or magnesium are given in the publication.

Further processes for preparing nickel-containing methanation catalysts by precipitating the active components from aqueous solution in the presence of a carrier material or by combined precipitation of the active constituents and the carrier materials from their solution are described for example in German Offenlegungsschrift Nos. 2 231 316; 2 231 367 and 2 261 634.

A further possibility of applying catalytically active components for the methanation onto carrier materials is to impregnate carriers having a large surface area. Thus, U.S. Pat. No. 3,933,883 describes a methanation catalyst which contains a nickel-cobalt mixed oxide on extremely pure $\gamma$-$Al_2O_3$ obtained by impregnating the carrier material with a solution containing nickel and cobalt salts, followed by calcination. However, the catalyst has an insufficient catalytic activity and is unsuitable for fluidized bed methanation.

Catalysts for fluidized bed methanation have been described in the proceedings "Evaluation of Fluidized Bed Methanation Catalysts" of the "8th Synthetic Pipeline Gas Symposium" of the "American Gas Association", "Energy Research and Development Administration" and "International Gas Union" 1976 in Monroeville, Pa., as well as in German Offenlegungsschrift No. 2 449 587. According to the above, finely particulate catalysts consisting of mixtures of nickel oxide with oxides of chromium, molybdenum and tungsten or of cobalt with chromium, molybdenum and tungsten oxides on aluminum oxide as carrier are used for simultaneous fluidized bed conversion and methanation. The preparation of the catalysts is not described. Additionally, the active life of 25 to 26 days achieved with the specified catalysts is unsatisfactory.

German Offenlegungsschrift No. 2 816 035 describes a fluidized bed catalyst for producing synthetic natural gas. The catalyst is prepared by mechanically mixing nickel oxide with carrier material and hydraulic cement as binder in a moistened state, followed by compressing the composition into shaped bodies which are first of all thermally treated and then comminuted to a particle size of 40 to 350 $\mu$m. The preparation of this catalyst is clearly very costly. With this catalyst too, a satisfactory active life cannot be obtained.

Special requirements are demanded of catalysts for fluidized bed methods. Additional requirements arise in the catalytic hydrogenation of carbon monoxide mainly resulting in methane. On account of the high gas velocities typical for fluidized bed reactions, resulting in short residence times of the reactants over the catalyst, the catalysts must have a high activity in order to ensure the rapid establishment of the reaction equilibrium.

In order to guarantee a satisfactory fluidization behaviour and thus a faultless technical operation, in addition specific requirements are placed on the mechanical properties of the catalyst, which principally concern its particle size distribution and density. An essential factor in evaluating a fluidized bed catalyst is also its mechanical resistance to abrasion and attrition. The amount of very fine material which has to be removed and extracted for operational reasons should be less than 1% by weight of the catalyst mass per operating day in order to keep the losses within tolerable limits (see e.g. A. Anderlohr, K. Hedden: GWF Gas, Erdgas 118, 422 (1977)).

For preparing methanation catalysts for fluidized bed methods, catalyst preparation by precipitation is disadvantageous for several reasons. The uniform deposition of the active components onto a carrier requires great care and is often difficult to reproduce. The catalyst precursor and the finished catalyst is usually obtained in a regular or irregular form, but not, however, in the particle size distribution required for use in fluidized bed methods. The measures adopted to obtain the desired particle size distribution inevitably result in an unavoidable incidence of fine and coarse particle fractions, which must be recycled to the production process or otherwise utilized, or considered as lost material. Considerable economic disadvantages thus result, especially in the case of catalysts containing large amounts of the expensive active components nickel and cobalt.

In order to achieve a technically and economically satisfactory operating time, the catalyst must also be sufficiently stable at high temperatures, i.e. roughly between 300° and 600° C.

The relatively high nickel and cobalt content of catalysts prepared by precipitation, amounting to roughly 30 to 60% by weight of the catalyst mass, leads to high costs when using these metals in methanation processes. A reduction in the concentrations of the active components nickel and cobalt to an economically more favorable level of e.g. less than 30% referred to the total catalyst results on the other hand in the case of precipitated catalysts in a marked drop in activity and useful operating time.

To summarize, it can thus be seen that a catalyst suitable for methanation of carbon monoxide in a fluidized bed method must in particular satisfy the following requirements:

It must have a high activity at the lowest possible concentration of the active components, and must also exhibit outstanding mechanical stability and satisfactory fluidization behaviour and be resistant to high temperatures. Its preparation should be simple and economical and should ensure the reproducibility of the desired catalyst properties.

Finally, the predominantly methane-containing gas mixture formed by hydrogenating carbon monoxide must be similar as regards composition to natural gas and should be largely free from unreacted carbon monoxide. In order to reduce the flame speed, an as low as possible hydrogen content is also desirable. A proportion of ethane, propane or butane in an overall range of 0.1 to 5% by vol. referred to methane raises the calorific value of the methane-rich gas and is thus desirable.

SUMMARY OF THE INVENTION

These and other objects are provided, in accordance with this invention, by a catalyst comprising cobalt, nickel and a carrier material, said catalyst additionally contains magnesium oxide.

The catalyst of the invention can be prepared by impregnating a carrier material with thermally decomposable salts of nickel, cobalt and magnesium, and thereafter fixing such salts to said support by drying the same and converting the salts into metal oxides by subsequent thermal treatment.

The catalysts according to the invention contain nickel, cobalt and magnesium in an atomic ratio of 1:0.05–0.5:0.05–0.5. The catalyst precursors obtained after the thermal treatment, in which the metals are present as oxides, contain 5–18% by weight of nickel, 0.25–9.0% by weight of cobalt and 0.10–3.73% by weight of magnesium, in each case based on the total catalyst mass including carrier.

The combination of nickel, cobalt and magnesium on suitable carrier materials is advantageous in many respect for methanation catalysts and is superior to the binary combinations of nickel and magnesium, cobalt and magnesium or nickel and cobalt on carriers. Presumably, the Ni—Co—Mg combinations involve a particularly uniform distribution of the three constituents among one another on account of mixed crystal formation. The almost statistical distribution of nickel, cobalt and magnesium is considered to be one of the reasons for the above-average performance of the catalysts prepared according to the invention.

The formation of compounds of the spinel type that occurs between nickel, cobalt and magnesium during the thermal treatment and under the methanation conditions increases the resistance of the active catalyst constituents to recrystallization, with the result that the new catalysts have long active lives.

Aluminum oxide, aluminum oxide-silicon dioxide combinations, for example in the form of aluminum silicates or aluminum oxide-silicon dioxide mixed oxides, or silicon dioxide, can be used as carrier materials. $\gamma Al_2O_3$ or aluminum oxide-silicon dioxide combinations containing 5–30, preferably 10–20% by weight of aluminum oxide, based on the total combination are preferred as carrier materials. The catalyst contains per 100 parts by weight of nickel—calculated as metal—300 to 1850 parts by weight, preferably 400–900 parts by weight, of carrier material. The claimed methanation catalysts are particularly suitable for use in fluidized bed methods.

Having regard to a good fluidizibility of the catalyst, the particle size distribution of the carrier material employed is preferably within the following ranges:

| Particle size range | % by weight of the carrier material |
|---|---|
| 32 μm | 10 |
| >32 μm–63 μm | 10–15 |
| >63 μm–80 μm | 15–25 |
| >80 μm–100 μm | 20–40 |
| >100 μm–125 μm | 30–50 |
| >125 μm–250 μm | 10–20 |

The bulk density or bulk weight of the carrier material, i.e. the weight of 1 liter of loose material (500–1200 g/l) is also important for the fluidization behaviour of the catalyst.

Carrier materials having surfaces of 130 to 600 m$^2$/g, preferably 150 to 300 m$^2$g, (determined by the BET method) are used for the catalysts prepared according to the invention. In order to be able to apply the specified concentrations of the active components, the carrier material should have a pore volume of more than 0.35 cm³/g. In order to use the catalysts according to the invention in a fluidized bed method, the pore volume of the carrier material should not exceed a value of 0.8 cm³/g since otherwise the abrasion resistance will generally be insufficient. Carrier materials that possess the required properties are commercially available.

The new catalysts are prepared by impregnating a carrier material having the afore-mentioned properties with a solution containing the thermally decomposable salts of nickel, cobalt and magnesium, preferably in the stated atomic ratio and in a concentration sufficient to ensure a content of 5 to 18% by weight of nickel in the catalyst after thermal treatment. The carrier material can be impregnated by steeping, by spray drying, or by a method similar to spray drying.

Solutions of compounds of nickel, cobalt and magnesium thermally decomposable to form the oxides, preferably the nitrates or acetates, and with an atomic ratio of the metals Ni:Co:Mg of for example 1:0.05 to 0.5:0.05 to 0.5, are used for impregnating the carrier materials. The metal concentration of the solutions is 50 to 300 g Ni/l. Nickel, cobalt and magnesium salts that are insufficiently soluble in the solvent in the given concentration range, for example formates or oxalates in water, are unsuitable. The solvent of the impregnating solution can be water, or an organic solvent, such as an alcohol, ketone or ether, in which the metal salts are soluble in the given concentration range.

In impregnating by steeping, the carrier material is introduced into the nickel-, cobalt- and magnesium-containing solution heated to 50°-100° C. The concentration of the solution should be 80-300 g nickel per liter, preferably 150-250 g of nickel per liter, and the impregnation time should be about 0.5 to 3 hours at a temperature of the suspension of 50°-100° C. The suspension is advantageously thoroughly mixed during the impregnation, the impregnated carrier is separated from the excess impregnation solution, for example by filtration, and is dried at elevated temperature, for example in the range from 50°-130° C. The excess impregnation solution, still containing nickel, cobalt and magnesium, may be reused for the impregnation after adjustment to the desired concentrations, so that there are no losses of the valuable metal salts.

For preparing the catalyst according to the invention by spray drying, a suspension of the above-described carrier materials in a solution containing nickel, cobalt and magnesium salts is similarly used. The atomic ratio of the metals present in the impregnation solution is, as in the first embodiment, Ni:Co:Mg=1:0.05-0.5:0.05-0.5. The concentration of the solution with respect to Ni is in the range from 50 to 280 g of nickel per liter, preferably between 100 and 250 g of nickel per liter. 300 to 1850 parts by weight of carrier material are used per 100 parts by weight of nickel. After allowing the metal salt solution to act on the carrier at 50° to 100° C. over a period of 0.5 to 2 hours, the suspension is distributed with the aid of a high speed sprayer and dried in a hot gas stream at temperatures of 90° to 350° C. If desired, a suitable binder, e.g. hydraulic cement, is added to the suspension in order to improve the abrasion resistance of the catalyst particles obtained in this way, though the addition of such a binder is not absolutely essential.

In the case of a method similar to spray drying, the carrier charged with metal salts is employed in the form of a moist pasty composition instead of a suspension, and is dried by mechanical distribution of the moist mass and fluidization in a hot gas stream. In this connection, the gas stream is at a temperature below the decomposition temperature of the employed metal salts into oxides, but is, however, sufficient for drying purposes. Temperatures in the range from 90°-300° C. are preferably used.

Metal salt solutions having an atomic ratio of the metals nickel, cobalt and magnesium of 1:0.05-0.5:0.05-0.5 may likewise be used. The concentration of the solution with reference to nickel is between 160 and 300 g of nickel per liter, preferably 200 to 250 g of nickel per liter. As carriers, the above-described materials are employed in amounts of 300-1850, preferably 400-900 parts by weight of carrier per 100 parts by weight of nickel calculated as metal. The concentration of the solution and the amount of carrier are adjusted with respect to one another so that a pasty to moist crumbly mass is obtained, the afore-mentioned ratio of amount of nickel to amount of carrier being adhered to.

The mixture of metal salt solution and carrier material is mixed for 0.5 to 2 hours at temperatures of 50° to 100° C. The moist mass is dried by gradually adding it to a rotor system in a hot gas stream and in this way the mass is comminuted and dried. The dried particles of the catalyst preproduct are transported from the drying zone by the hot gas stream and separated in a cyclone.

The catalyst precursors obtained from impregnation of carrier materials by steeping, spray drying or methods similar to spray drying are thermally treated to convert the metal salts into oxides. This thermal treatment is carried out between 300° and 650° C., preferably between 400° and 600° C., in the presence of nitrogen, oxygen or a mixture thereof, e.g. air. The duration of the thermal treatment is 0.5 to 5 hours, preferable 1 to 3 hours. The metal content of the oxidic catalyst preproducts obtained according to the described methods by steeping, spray drying or comminution in a hot air stream and after thermal treatment is 5 to 18% by weight of Ni, 0.25-9.0% by weight of Co, and 0.10-3.73% by weight of Mg.

The oxidic catalyst preproduct may be activated stationary, in a fluidized bed outside the methanation reactor, or "in situ" in the fluidized bed methanation reactor itself. Reduction is carried out at 350° to 500° C. with pure hydrogen or hydrogen-containing gases. The catalysts prepared and having the compositions according to the invention have outstanding mechanical and catalytic properties for the methanation of carbon monoxide, in particular by fluidized bed method.

The catalyst of the invention can be used for methanization reactions wherein hydrogen reacts with carbon monoxide to form methane. Generally speaking, these reactions are carried out at a temperature of between 200° and 750° C. preferably between 300° and 600° C. at pressures of between 1 and 150, preferably between 10 and 80 atmospheres. The gaseous hourly space velocity of the gases through the zone containing catalyst ranges from between 500 and 50.000 volumes (NTP) gas per volume of catalyst per hour, depending upon the catalyst and particular mode for carrying out the process. It is preferred that the methanization be conducted using a fluidized bed technique wherein the gases fluidize the catalysts and the same pass through a fluidized bed reactor. The catalyst particles are recycled together with fresh feed while the gaseous products are removed and stored. The known techniques of fluidized bed reactions are applicable to fluidized bed procedures employing the catalyst of the invention.

In order to more fully illustrate the nature of the invention and the amount of practice in the same and in order to compare the performance of the catalyst of the invention prepared by the process described herein, the following examples are presented. The examples which follow include comparative examples.

COMPARISON EXAMPLE 1

247.5 g Ni(NO$_3$).6H$_2$O and 65.8 g of Mg(NO$_3$)$_2$.6H$_2$O are dissolved in 130 ml of water to prepare a cobalt-free, magnesium-containing nickel impregnated catalyst. The solution is heated to 80° C. 100 g of Al$_2$O$_3$.SiO$_2$ carrier material (termed: L.A.C. and produced by AKZO Limited) is added to the solution while stirring, and the suspension obtained is stirred for 60 minutes at 80° C. The suspension is worked up by filtration, drying and calcination as per Example 1. The calcined catalyst preproduct has essentially the same particle distribution given in Example 1, and contains 13.8% by weight of nickel and 1.3% by weight of MgO (referred to the total mass).

Reduction is carried out as per Example 1. The methanation is carried out in the same apparatus and under the same conditions as in Example 1.

Feedstock gas: 68.0% by vol. H$_2$; 30.8% by vol. CO
Temperature in the reaction zone: 410°–412° C.
Reaction mixture (without water): 53.3% by vol. CH$_4$; 19.5% by vol. CO$_2$; 23.7% by vol. H$_2$, and 2.3% by vol. CO.

EXAMPLE 1

To prepare a cobalt-and magnesium-containing nickel impregnated catalyst, 247.5 g og Ni(NO$_3$)$_2$.6H$_2$O, 49.4 g of Co (NO$_3$)$_2$.6H$_2$O and 65.8 g of Mg(NO$_3$)$_2$.6H$_2$O are dissolved in 130 ml of water and the solution is heated to 80° C. 100 g of Al$_2$O$_3$.SiO$_2$ carrier (description: L.A.C.-25-C produced by AKZO Limited) is added to the solution while stirring, and the suspension obtain is stirred for 60 minutes at 80° C. After separating the impregnation solution by filtration, the moist cake charged with Ni, Co and Mg nitrates is dried for 16 hours at 110° C. and the resultant dry product is then calcined for 2 hours at 500° C.

A finely-divided, fluidizable catalyst preproduct having the following particle size distribution is obtained:

| | |
|---|---|
| 32 μm | 6.4% |
| >32–63 μm | 11.4% |
| >63–80 μm | 24.3% |
| >80–100 μm | 36.6% |
| >100–125 μm | 18.7% |
| >125–250 μm | 2.6% |

The calcined product contains 11.7% by weight Ni, 2.4% by weight Co and 1.2% by weight MgO, referred to the total mass.

This catalyst preproduct is reduced in a stream of hydrogen in the fluidized bed for 2 hours at 450° C., at an hourly H$_2$ throughput of 1 liter of H$_2$ per 1 ml of catalyst bulk material.

A gas mixture (68.0% by vol. H$_2$, 30.8% by vol. CO, and approx. 0.2% by vol. N$_2$) is used for the methanation. The methanation tests are carried out at normal pressure with 20 ml of catalyst bulk material in a vertically arranged, electrically heated tube having a gas-permeable floor (frit). The furnace jacket temperature is adjusted to 380° C. In order to generate a fluidized bed, 20 l of carbon monoxide-hydrogen mixture of the aforementioned composition are passed per hour through the catalyst layer. A temperature of 412° to 415° C. is established in the fluidized bed. The dried gas mixture flowing from the reactor has the following composition:

59.8% by vol. CH$_4$; 20.2% by vol. CO$_2$;
17.9% by vol. H$_2$; 0.6% by vol. CO;
remainder N$_2$.

According to thermodynamic equilibrium calculations, the following gas composition (without water) is obtained starting from a feedstock gas having the aforementioned composition (H$_2$/CO = 2.2) for the measured reaction temperature of 415° C. and total pressure $P_{abs.} = 1$ bar:

59.4% by vol. CH$_4$; 21.9% by vol. CO$_2$;
16.9% by vol. H$_2$; and 1.3% by vol. CO.

In the calculation it is assumed that no carbon deposition takes place.

The substantial agreement between the gas composition determined experimentally and that calculated thermodynamically illustrates the high efficiency of the catalyst according to the invention.

COMPARISON EXAMPLE 2

247.5 g of Ni(NO$_3$)$_2$.6H$_2$O and 49.5 g of Co(NO$_3$)$_2$.6H$_2$O are dissolved in 130 ml of water to prepare a magnesium-free, cobalt-containing nickel impregnated catalyst whose carrier material corresponds to that given in Example 1. The solution is heated to 80° C. 100 g of Al$_2$O$_3$.SiO$_2$ carrier material (description: L.A.C. produced by AKZO Limited) is added to the solution and the suspension obtained is stirred for 60 minutes at 80° C. The suspension is worked up by filtration, drying and calcination as per Example 1. The calcined catalyst preproduct has essentially the same particle size distribution as given in Example 1 and contains 12.3% by weight Ni and 2.2% by weight Co (referred to the total mass).

The reduction corresponds to the procedure in Example 1. Methanation is carried out in the same apparatus and under the same conditions as in Example 1.

Feedstock gas: 67.5% by vol. CO: 31.6% by vol. H$_2$;
Temperature in the reaction zone: 415° C.
Reaction mixture (without water): 54.1% by vol. CH$_4$; 21.2% by vol. CO$_2$; 21.3% by vol. H$_2$; 2.4% by vol. CO; approx. 1% by vol. N$_2$.

EXAMPLE 2

171.3 g of Ni(NO$_3$)$_2$.6H$_2$O, 35.1 g of Co (NO$_3$)$_2$.6H$_2$O and 44.1 g of Mg(NO$_3$)$_2$.6H$_2$O are dissolved in 95 ml of water to prepare a cobalt-containing and magnesium-containing nickel impregnated catalyst whose carrier material consists essentially of γ-Al$_2$O$_3$ (Al$_2$O$_3$ type A produced by Martinswerk Limited). The solution is heated to 80° C. 120 g of the Al$_2$O$_3$ carrier material is added to the solution (170 ml) while stirring, and the suspension obtained is stirred for 60 minutes at 80° C. The suspension is worked up by filtration, drying and calcination as per Example 1. The calcined catalyst preproduct essentially has the particle size distribution corresponding to the carrier material, and contains 8.4% by weight Ni, 1.6% by weight Co and 0.9% by weight Mg (referred to the total mass).

| | |
|---|---|
| 32 μm | 10% |
| >32–63 μm | 10% |
| >63–80 μm | 20% |
| >80–100 μm | 27% |
| >100–125 μm | 23% |

| | |
|---|---|
| >125 μm | 10% |

The reduction corresponds to the procedure of Example 1. The methanation is carried out in the same apparatus and under the same conditions as in Example 1.

Feedstock gas: 70.5% by vol. $H_2$; 28.2% by vol. CO;
Temperature in the reaction zone: 435° C.
Reaction mixture (without water): 58.3% by vol. $CH_4$; 19.3% by vol. $CO_2$; 21.0% by vol. $H_2$; 0.4% by vol. CO Thermodynamically calculated value: 58.3% by vol. $CH_4$.

EXAMPLE 3

940 g of $Ni(NO_3)_2.6H_2O$, 90 g of $Co(NO_3)_2.6H_2O$ and 120 g of $Mg(NO_3)_2.6H_2O$ are dissolved in 900 ml of water to prepare a cobalt- and magnesium-containing nickel methanation catalyst dried by means of spray drying. The solution is heated to 80° C. 1200 g of $Al_2O_3$ carrier material essentially consisting of $\gamma$-$Al_2O_3$ ($Al_2O_3$ type A produced by Martinswerk Limited) is added to the solution while stirring, and the suspension obtained is stirred for 30 minutes at 80° C. The suspension is then sprayed with the aid of a rotating sprayer operating at approx. 20,000 revs./minute in an air stream heated to 260°–300° C. (spray drying) and dried.

The dry product is calcined according to Example 1. The calcined catalyst preproduct essentially has the particle size distribution corresponding to the carrier material, and contains 12.2% by weight Ni, 1.2% by weight Co and 1.1% by weight Mg (referred to the total mass).

The reduction corresponds to the procedure described in Example 1. The methanation is carried out in the same apparatus and under the same conditions of Example 1.

Feedstock gas: 70.5% by vol. $H_2$; 29.5% by vol. CO; remainder $N_2$
Temperature in the reaction zone: 430° C.
Reaction mixture (without water): 58.4% by vol. $CH_4$; 19.5% by vol. $CO_2$; 20.8% by vol. $H_2$; 0.3% by vol. CO; 0.9% by vol. $N_2$ Thermodynamically calculated values: 58.7% by vol. $CH_4$; 19.3% by vol. $CO_2$; 20.6% by vol. $H_2$; 0.3% by vol. CO.

EXAMPLE 4

79.4 g of $Ni(NO_3)_2.6H_2O$, 8.1 g of $Co(NO_3)_2.6H_2O$ and 10.3 g $Mg(NO_3)_2.6H_2O$ are dissolved in 27.4 ml of water to prepare a cobalt- and magnesium-containing nickel methanation catalyst, which is dried by a method similar to spray drying. The solution is heated to 80° C. 134 g of $Al_2O_3$ (type A produced by Martinswerk Limited; $\gamma$-$Al_2O_3$) is added to the solution while stirring, a moist, pasty mass being obtained, which is dried after being allowed to stand for 45 minutes by means of a method similar to spray drying. In this connection, the moist, pasty mass is fed by means of a screw conveyor to a rotor system installed in the lower part of a cylindrical vessel. Hot air is at the same time passed through the fluidized product. Calcination is carried out according to Example 1.

The calcined catalyst preproduct essentially has the particle size distribution corresponding to that of the carrier material and contains 10% by weight Ni, 1.1% by weight Co and 0.9% by weight Mg (referred to the total mass).

The reduction corresponds to the procedure given in Example 1. The methanation is carried out in the same apparatus and under the same conditions as in Example 1.

Feedstock gas: 70.5% by vol. $H_2$; 29.5% by vol. CO
Temperature in the reaction zone: 430° C.
Reaction mixture (without water): 58.8% by vol $CH_4$; 19.3% by vol. $CO_2$; 20.7% by vol. $H_2$; and 0.3% by vol. CO.

What is claimed is:

1. A methanation catalyst comprising cobalt, nickel and magnesium, disposed on a carrier.

2. A methanation catalyst according to claim 1, wherein the atomic ratio of nickel to cobalt to magnesium is in a range of 1:0.05 to 0.5:0.05 to 0.5.

3. A methanation catalyst according to claim 1, wherein the said carrier comprises aluminum oxide, an aluminum oxide-silicon oxide combination, aluminum silicate, a mixed oxide of aluminum oxide and silicon-dioxide or silicon dioxide.

4. A methanation catalyst according to claim 3, wherein said carrier comprises gamma alumina.

5. A methanation catalyst according to claim 3, wherein said catalyst comprises a combination of aluminum oxide and silicon dioxide, said catalyst containing 5 to 30% by weight of aluminum oxide, based upon the total weight of the carrier.

6. A methanation catalyst according to claim 5, wherein said carrier contains 10 to 20% by weight aluminum oxide.

7. A methanation catalyst according to claim 1, wherein said catalyst comprises 300 to 1850 parts by weight carrier per 100 parts by weight nickel metal.

8. A methanation catalyst according to claim 2, wherein there are 300 to 1850 parts by weight of carrier per 100 parts by weight of nickel metal.

9. A methanation catalyst according to claim 2, wherein there are 400 to 900 parts by weight carrier per 100 parts by weight nickel metal.

10. A methanation catalyst according to claim 1, wherein the said carrier has a surface area of 130 to 600 square meters per gram and a pore volume of more than 0.35 cubic centimeters per gram.

11. A methanation catalyst according to claim 1, containing 5–18 weight percent nickel, 0.25 to 9.0 weight percent cobalt and 0.10–3.73 weight percent magnesium, based upon the total weight of the catalyst including the weight of the carrier.

12. A methanation catalyst according to claim 1, suitable for use in fluidized bed methanation having a particle size of less than 250 μm.

13. A methanation catalyst according to claim 12, wherein said catalyst have a particle size less than 125 μm.

14. A methanation catalyst according to claim 1, wherein said catalyst has a particle size of less than 100 μm.

15. A methanation catalyst according to claim 1, wherein said catalyst has a particle size of less than 80 μm.

16. A methanation catalyst according to claim 1, suitable for use in fluidized bed methanation having a particle size distribution in accordance with the following ranges:

| Particle size range | % by weight of the carrier material |
|---|---|
| 32 μm | 10 |
| >32 μm–63 μm | 10–15 |
| >63 μm–80 μm | 15–25 |

-continued

| Particle size range | % by weight of the carrier material |
|---|---|
| >80 μm–100 μm | 20–40 |
| >100 μm–125 μm | 30–50 |
| >125 μm–250 μm | 10–20 |

17. A methanation catalyst according to claim 12, having a bulk density of 500 to 1200 g/l.

* * * * *